(12) United States Patent  
Brunfeld et al.

(10) Patent No.: US 8,436,997 B2
(45) Date of Patent: May 7, 2013

(54) OPTICAL INSPECTION SYSTEM WITH POLARIZATION ISOLATION OF DETECTION SYSTEM REFLECTIONS

(75) Inventors: Andrei Brunfeld, Cupertino, CA (US); Gregory Toker, Jerusalem, IL (US); Bryan Clark, Mountain View, CA (US)

(73) Assignee: Xyratex Technology Limited, Havant, Hampshire (GB)

( * ) Notice: Subject to any disclaimer, the term of this patent is extended or adjusted under 35 U.S.C. 154(b) by 327 days.

(21) Appl. No.: 12/971,334

(22) Filed: Dec. 17, 2010

(65) Prior Publication Data

US 2012/0154806 A1 Jun. 21, 2012

(51) Int. Cl.
*G01J 4/00* (2006.01)

(52) U.S. Cl.
USPC .......................................................... 356/369

(58) Field of Classification Search .................... 356/369
See application file for complete search history.

(56) References Cited

U.S. PATENT DOCUMENTS

| | | | |
|---|---|---|---|
| 4,669,875 A * | 6/1987 | Shiba et al. | ................. 356/237.3 |
| 4,770,505 A | 9/1988 | Okazaki | |
| 4,902,134 A | 2/1990 | Spanier | |
| 5,033,830 A | 7/1991 | Jameson | |
| RE33,991 E * | 7/1992 | Shiba et al. | ................. 356/237.3 |
| 5,440,383 A | 8/1995 | Bacchus et al. | |
| 5,875,029 A | 2/1999 | Jann et al. | |
| 6,977,763 B1 | 12/2005 | Wang et al. | |
| 7,006,224 B2 * | 2/2006 | Some | ............................. 356/369 |
| 7,110,106 B2 * | 9/2006 | Xu et al. | ..................... 356/237.5 |
| 7,330,277 B2 * | 2/2008 | Brunfeld et al. | .............. 356/519 |
| 7,433,031 B2 * | 10/2008 | Xu et al. | ..................... 356/237.2 |
| 7,619,746 B2 | 11/2009 | De Lega | |
| 7,671,978 B2 * | 3/2010 | Clark et al. | ....................... 356/73 |
| 7,826,047 B2 | 11/2010 | Shibata et al. | |
| 2002/0039436 A1 * | 4/2002 | Alumot et al. | ................ 382/149 |
| 2004/0125375 A1 * | 7/2004 | Some | ............................. 356/369 |
| 2005/0094136 A1 * | 5/2005 | Xu et al. | ..................... 356/237.3 |
| 2005/0094864 A1 * | 5/2005 | Xu et al. | ....................... 382/145 |
| 2005/0105791 A1 * | 5/2005 | Lee et al. | ....................... 382/145 |
| 2009/0116023 A1 | 5/2009 | Wadman | |
| 2009/0296096 A1 | 12/2009 | Jeong | |
| 2012/0019816 A1 * | 1/2012 | Shibata et al. | ............. 356/237.5 |

OTHER PUBLICATIONS

U.S. Appl. No. 12/877,480, filed Sep. 8, 2010, Brunfeld, et al.
U.S. Appl. No. 12/877,527, filed Sep. 8, 2010, Brunfeld, et al.

* cited by examiner

*Primary Examiner* — Roy M Punnoose
(74) *Attorney, Agent, or Firm* — Mitch, Harris, Atty at Law, LLC; Andrew M. Harris

(57) ABSTRACT

An optical inspection system includes a polarizing isolator that reduces error in measurements by preventing ghost light reflected or scattered from element of a detection subsystem from re-entering the illumination and detection optical paths. The polarizing isolator may include a polarizing splitter that isolates light directionally according the a linear polarization state and two quarter-wave plates for transforming linearly polarized light to circularly polarized light.

20 Claims, 4 Drawing Sheets

OPTICAL INSPECTION SYSTEM WITH POLARIZATION ISOLATION OF DETECTION SYSTEM REFLECTIONS

BACKGROUND OF THE INVENTION

1. Field of the Invention

This invention relates to optical measurement and inspection systems, and more specifically, to an optical inspection head and system in which light reflected from a detection optical path is isolated from the illumination and other detection optical paths.

2. Background of the Invention

Optical surface inspection systems are in common use in industry for both analysis and manufacturing test operations. The optical heads used to provide measurements when scanning a surface may combine multiple types of detection. For example, U.S. Pat. No. 7,671,978, issued to the inventors of the present application, discloses optical heads that include both an interferometer and a scatterometer channel. In other applications, single channel systems are used.

Dark field detectors are sensitive to stray light sources and leakage along the optical path. In particular, scattering detectors or scatterometers, are extremely sensitive to parasitic light originating in so-called "ghost images" in the optical system, and to reflection and re-scattering of ambient light. Light reflecting from the dark-field detection subsystem, or an additional bright field detection subsystem can re-enter the optical measurement system and enter (or re-enter) the dark-field detection channel via reflections from optical system components such as lenses and beam-splitters, and also potentially from the surface under inspection.

Therefore, it would be desirable to provide a dark field scattering detection system that prevents light that enters a detection subsystem from being reintroduced to the optical inspection system.

SUMMARY OF THE INVENTION

The foregoing objectives are achieved in an optical inspection system and a method of operation of the optical inspection system. The optical inspection system includes a polarizing isolator that reduces error in measurements by preventing ghost light reflected or scattered from element of a detection subsystem from re-entering the illumination and detection optical paths.

The polarizing isolator may include a polarizing splitter that isolates light directionally according the a linear polarization state and two quarter-wave plates for transforming linearly polarized light to circularly polarized light.

The foregoing and other objects, features, and advantages of the invention will be apparent from the following, more particular, description of the preferred embodiment of the invention, as illustrated in the accompanying drawings.

DESCRIPTION OF ILLUSTRATIVE EMBODIMENT

The present invention encompasses optical inspection systems in which reflections from a detection apparatus are prevented from re-entering the optical system, thereby removing sources of error from ghost reflections from components in the detection apparatus, including reflections from the detector element itself.

Figure 1:
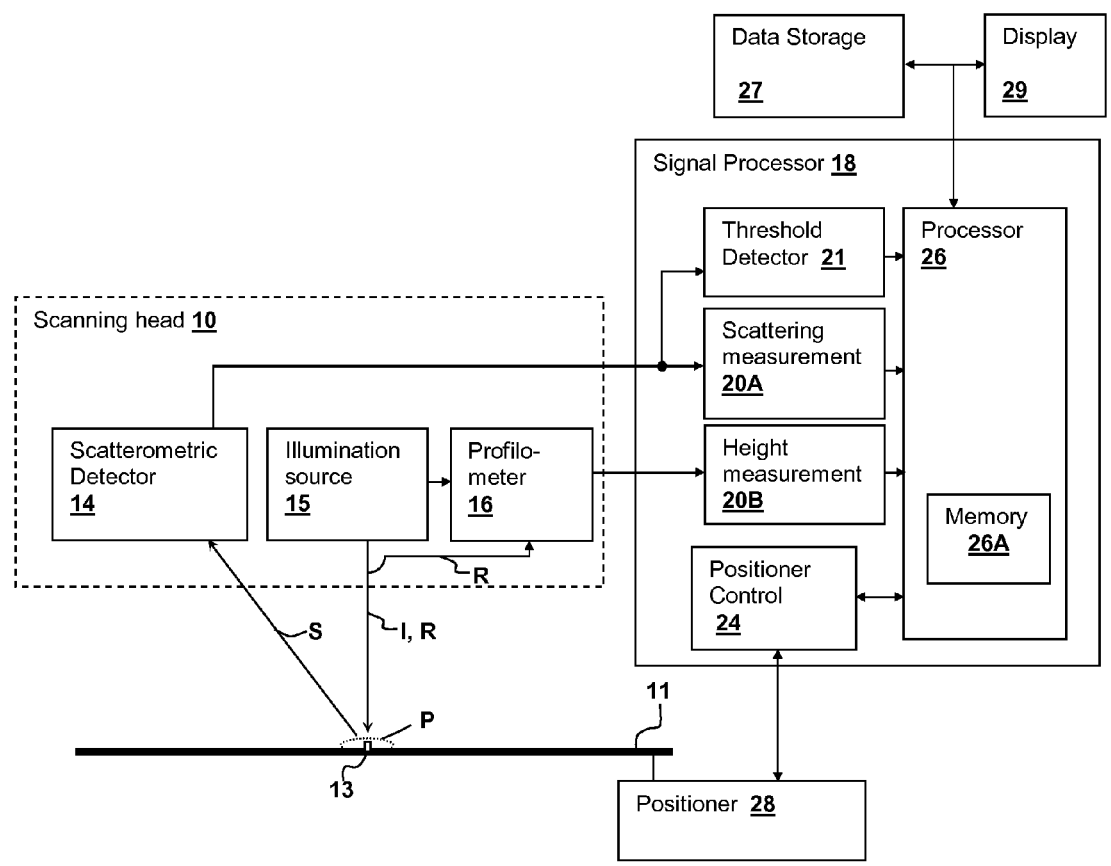
FIG. 1 is a block diagram depicting an optical inspection system in which an embodiment of the present invention is practiced.

Referring now to FIG. 1, an optical inspection system in which an embodiment of the present invention is practiced, is shown. A scanning head 10 is positioned over a surface under inspection 11, which is moved via a positioner 28 that is coupled to a signal processor 18. From scanning head 10, illumination I of surface under inspection 11 is provided by an illumination source 15. A scattering detector 14 receives light scattered from surface under inspection 11 along optical path S from an illumination spot P generated by illumination I. Scatterometric optical path S gathers light from one or more non-specular angles with respect to illumination I and surface under inspection 11, so that light scattered from an artifact 13 (which may be a surface defect or feature, or an extraneous particle) disposed on surface under inspection 11, indicates the presence of the artifact. A profilometer 16 is included, such as an interferometer channel that interferes reflected light R returning along the illumination path, or another optical path and combines the reflected light R with light directly coupled from illumination source 15 to determine the height of surface under inspection 11 within illumination spot P.

While the illustration shows a positioner 28 for moving surface under inspection under scanning head 10, it is understood that scanning head 10 can be moved over a fixed surface, or that multiple positioners may be employed, so that both scanning head 10 and surface under inspection 11 may be moved in the measurement process. Further, while scattering detector 14 and illumination source 15 are shown as included within scanning head 10, optical fibers and other optical pathways may be provided for locating scattering detector 14 and illumination source(s) 15 physically apart from scanning head 10.

Signal processor 18 includes a processor 26 that includes a memory 26A for storing program instructions and data. The program instructions include program instructions for controlling positioner 28 via a positioner control circuit 24, and performing measurements in accordance with the output of scatterometric detector 14 via scatterometer measurement circuit 20A that include signal processing and analog-to-digital conversion elements as needed for receiving the output of scatterometric detector 14. Profilometer channel 16 is coupled to a height measurement circuit 20B that provides an output to processor 26. A dedicated threshold detector 21 can be employed to indicate to processor 26 when scattering from an artifact 13 on surface under measurement 11 has been detected above a threshold. As an alternative, continuous data collection may be employed. Processor 26 is also coupled to an external storage 27 for storing measurement data and a display device 29 for displaying measurement results, by a bus or network connection. External storage 27 and display device 29 may be included in an external workstation computer or network connected to the optical inspection system of the present invention by a wired or wireless connection.

Figure 2:
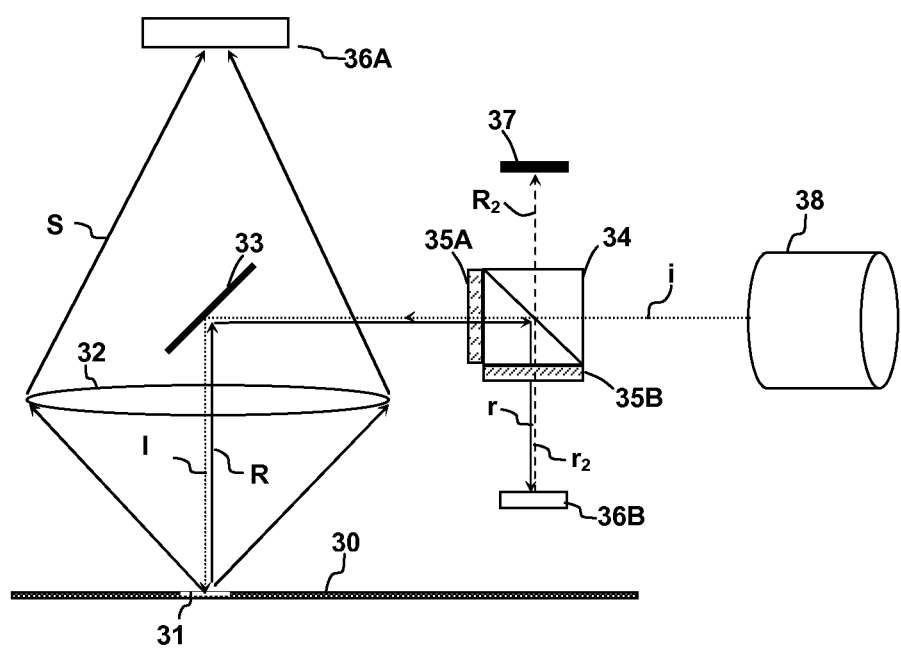
FIG. 2 is a pictorial diagram depicting an optical system in accordance with an embodiment of the present invention.

Referring now to FIG. 2, an optical system in accordance with another embodiment of the present invention is shown, which may be implemented in the optical inspection system of FIG. 1. In the depicted embodiment, an illumination source 38 directs illumination I to surface under inspection 30 through a polarizing isolator 34 that first converts illumination I to plane-polarized light and includes a first quarter-wave plate 35A that introduces a 45-degree shift between the polarization states. The resulting circularly polarized illumination I is further directed to surface under inspection by a polarization-neutral bending mirror 33, to produce an illumination spot 31 on surface under inspection. Light S scattered by artifacts within illumination spot 31 is collected by collecting lens 32, which may have a large numerical aperture. Light S collected by collecting lens 32 is directed to a detector 36A, which may be a point detector, or an array of detection elements in one or two dimensions, a focal plane array, a linear array of individual detectors such as avalanche photodiodes, a coherent fiber optics bundle that is coupled to a detector array or individual detectors, a microchannel image intensifier plate (MCP), or another suitable optical detector or detector array, which implement scatterometric detector 14 of FIG. 1.

Profilometer 16 of FIG. 1 is implemented in the optical system of FIG. 2 by a detector 36B, which may be a bright-field interferometer, a deflectometer or another suitable measurement subsystem for measuring a characteristic of the light R specularly reflected by surface of interest 30. The circularly-polarized reflected light R passes again through first quarter-wave plate 35A and is transformed into linearly-polarized light r, which is reflected by polarizing isolator 34 toward detector 36B. Since the linearly polarized light r is rotated 90 degrees with respect to illumination I (assuming that the reflection at surface under inspection 30 has an insubstantial imaginary component), polarizing isolator 34 will direct reflected light r to detector 36B, rather than toward illumination source 38. Reflected light r passes through a second quarter-wave plate 35B, which transforms reflected light r to circularly polarized light, which is then provided to detector 36B. Light r2 reflected from detector 36B, which includes reflections from any optical component along the optical path from second quarter-wave plate 35B to the detection element, is transformed to linearly polarized light $R_2$ by second quarter-wave plate 35B, and due to the rotation of light $r_2$ upon reflection from detector 36B, exits polarizing isolator in the direction of optical trap 37, rather than being emitted along the direction of illumination I. Thus, polarizing isolator 34 provides elimination of error due to ghost light reflected from optical system components, and any other reflective structures or detritus, between polarizing isolator 34 and detector 36B. Otherwise, light $r_2$ could re-enter the optical system, reaching either collection lens 32 or surface under inspection 30, and being scattered through collecting lens 32 into dark-field detector 36A.

Figure 3A:
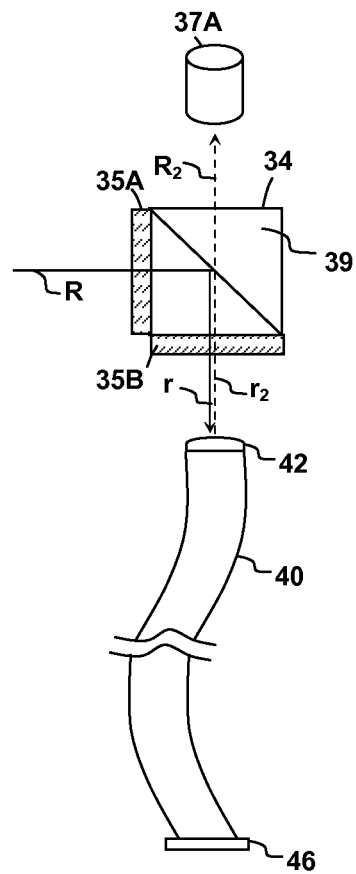
FIG. 3A is a pictorial diagram depicting an optical system in accordance with another embodiment of the present invention.

Referring now to FIG. 3A, details of an optical system in accordance with an embodiment of the invention, as may implement the optical system of FIG. 2 is shown. The detection apparatus for the profilometer channel includes an optical fiber waveguide 40, which has an end shaped as a lens 42 for receiving reflected light r from surface under inspection 30. Polarizing isolator 34 is constructed as shown in FIG. 2, from a partially reflective mirror 39, and two 45-degree oriented quarter-wave plates 35A-35B. Reflected light $r_2$ includes light reflected from lens 42, as well as all of the cumulative internal reflections of optical fiber waveguide that result in light exiting lens 42 in the direction of polarizing isolator 34, as well as any reflections from a detector 46 coupled to the distal end of optical fiber waveguide 40 that are guided back through optical fiber waveguide 40 and emitted from lens 42 in the direction of polarizing isolator 34. Reflected light $R_2$ is absorbed by an optical trap 37A, which may include baffles, absorbing surfaces, mirrors and other structures that prevent reflections of reflected light $R_2$ back into the optical system, i.e., reflected in the direction of polarizing isolator 34.

Figure 3B:
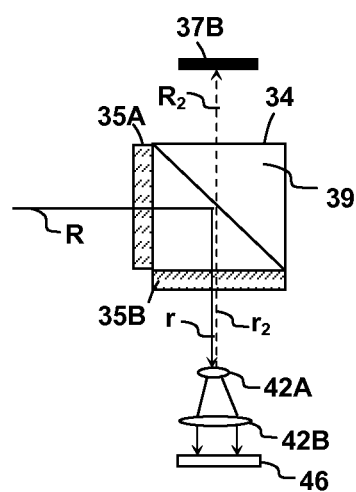
FIG. 3B is a pictorial diagram depicting an optical systems in accordance with yet another embodiment of the present invention.

Referring now to FIG. 3B, details of an optical system in accordance with another embodiment of the invention, as may implement the optical system of FIG. 2 is shown. The detection apparatus for the profilometer channel includes a lens system formed by lenses 42A and 46B that image reflected light r from surface under inspection 30 onto detector 46. Polarizing isolator 34 is constructed as shown in FIG. 2, from a partially reflective mirror 39, and two 45-degree oriented quarter-wave plates 35A-35B. Reflected light $r_2$ includes light reflected from lenses 42A-42B, as well as any reflections from a detector 46. Reflected light $R_2$ is absorbed by an optical trap 37B, which is illustrated as an absorbing sheet that prevent reflections of reflected light $R_2$ back into the optical system, i.e., reflected in the direction of polarizing isolator 34.

While the above-illustrated examples show circularly polarized light being used to detect artifacts on surface of interest 30 and isolation of linearly-polarized light after transformation by quarter-wave plates 35A-35B, polarization isolation can be performed on the circularly polarized light and/or linearly polarized light can be used to perform the detection of artifacts on surface of interest 30, in other embodiments of the invention that use Faraday Rotators and/or bi-refringent wedge structures to operate entirely in the linear or circular polarized light domains, or in another combined circular/linear isolation scheme similar to that illustrated above.

While the invention has been particularly shown and described with reference to the preferred embodiments thereof, it will be understood by those skilled in the art that the foregoing and other changes in form and details may be made therein without departing from the spirit and scope of the invention.

What is claimed is:

1. An optical system, comprising:
   an illumination subsystem for providing a source of coherent light;
   a first optical detector for detecting light reflected from a surface under inspection; and
   a polarizing isolator for polarizing the coherent light provided by the illumination subsystem and directing resulting polarized light having a first polarization state along an illumination optical path to generate a spot on the surface under inspection, wherein the polarizing isolator further couples the reflected light returning along the illumination optical path to the first optical detector along a detection optical path directed away from the illumination subsystem and wherein the polarizing isolator further comprises a second polarizing element that directs reflections from the detection optical path to an isolated optical path away from the illumination optical path, whereby light reflected from structures along the detection optical path is prevented from re-entering the illumination optical path.

2. The optical system of claim 1, further comprising an optical trap disposed along the isolated optical path for preventing re-reflection of the reflections from the illumination optical path that are directed to the isolated optical path.

3. The optical system of claim 2, wherein the optical trap is an optical absorbing element disposed along the isolated optical path.

4. The optical system of claim 1, wherein the detection optical path comprises an optical fiber coupled to the polarizing isolator at a first end thereof and the first optical detector at a second end thereof.

5. The optical system of claim 1, wherein the first optical detector forms part of an interferometer.

6. The optical system of claim 1, wherein the first optical detector forms part of a deflectometer.

7. The optical system of claim 1, wherein the polarizing isolator comprises:
a polarizing splitter;
a first quarter-wave plate disposed between the polarizing splitter and the surface under inspection; and
a second quarter-wave plate disposed between the polarizing splitter and the first optical detector.

8. The optical system of claim 7, wherein the polarizing splitter is oriented at forty-five degree angles with respect to the illumination optical path and the detection optical path, wherein the detection optical path and the isolated optical path are oriented at right angles with respect to each other and wherein the first quarter-wave plate and the second quarter-wave plate are oriented at right angles with respect to each other.

9. The optical system of claim 1, further comprising:
a collecting lens disposed along the illumination optical path and disposed between the surface under inspection and the polarizing isolator; and
a second optical detector for receiving light scattered from the surface under inspection and collected by the collecting lens.

10. The optical system of claim 9, wherein the collecting lens has an optical axis oriented at a predetermined angle with respect to the surface under inspection, and further comprising a bending mirror located along the optical axis of the collecting lens between the collecting lens and the second optical detector, for directing light reflected from the surface under inspection toward the polarizing isolator.

11. The optical system of claim 10, wherein the predetermined angle is normal to the surface under inspection.

12. A method of operating an optical inspection system, comprising:
illuminating a surface under inspection with polarized light;
receiving light returned from the surface under inspection at a detection apparatus of the optical inspection system; and
isolating light reflected from the detection apparatus to prevent the light reflected from the detection apparatus from re-entering the optical inspection system, using a polarizing isolator.

13. The method of claim 12, wherein the further comprising directing the isolated light to an optical absorber.

14. The method of claim 12, wherein the receiving receives the light from an interferometer channel.

15. The method of claim 12, wherein the receiving receives the light from a deflectometer channel.

16. The method of claim 12, wherein the illuminating is performed through the polarizing isolator and wherein the method further comprises:
linearly polarizing the polarized light with a polarizing splitter to provide first linearly polarized light;
transforming the first linearly polarized light to first circularly polarized light using a first quarter-wave plate disposed between the polarizing splitter and the surface under inspection, wherein the illuminating illuminates the surface with the first circularly polarized light; and
transforming second circularly polarized light reflected from the detection apparatus to second linearly polarized light with a second quarter-wave plate disposed between the polarizing splitter and the first optical detector, and wherein the isolating is performed by the polarizing splitter directing the second linearly polarized light in a direction away from the direction of the light returned from the surface under inspection.

17. The method of claim 12, further comprising:
collecting light scattered from the surface under inspection using a collecting lens between the surface under inspection and the polarizing isolator; and
receiving light scattered from the surface under inspection and collected by the collecting lens at another detection apparatus of the optical inspection system.

18. The method of claim 17, wherein the collecting lens has an optical axis oriented at a predetermined angle with respect to the surface under inspection, and further comprising directing light reflected from the surface under inspection toward the polarizing isolator using a bending mirror located along an optical axis of the collecting lens and disposed between the collecting lens and the second optical detector.

19. The method of claim 18, wherein the predetermined angle is normal to the surface under inspection.

20. An optical inspection system, comprising:
an illumination subsystem for providing a source of coherent light;
an optical detection apparatus for detecting light reflected from a surface under inspection;
a polarizing splitter disposed between the illumination subsystem and the surface under inspection for linearly polarizing the coherent light to produce first circularly polarized light;
a first quarter-wave plate disposed between the polarizing splitter and the surface under inspection for circularly polarizing the first linearly polarized light; and
a second quarter-wave plate disposed between the polarizing splitter and the optical detection apparatus for transforming circularly polarized light reflected from the surface under inspection to second linearly polarized light, wherein the polarizing splitter directs light reflected from the optical detection apparatus away from the surface under inspection and the illumination subsystem.

\* \* \* \* \*